(12) United States Patent
Mautner et al.

(10) Patent No.: US 9,334,293 B2
(45) Date of Patent: May 10, 2016

(54) METHOD FOR PRODUCING ALKYL CHLOROSILANES BY WAY OF REARRANGEMENT REACTIONS

(71) Applicant: Wacker Chemie AG, Munich (DE)

(72) Inventors: Konrad Mautner, Burghausen (DE);
Werner Geissler, Thiendorf (DE);
Volker Hoellein, Burghausen (DE);
Gudrun Tamme, Mortizburg (DE)

(73) Assignee: WACKER CHEMIE AG, Munich (DE)

( * ) Notice: Subject to any disclaimer, the term of this patent is extended or adjusted under 35 U.S.C. 154(b) by 0 days.

(21) Appl. No.: 14/761,527

(22) PCT Filed: Jan. 2, 2014

(86) PCT No.: PCT/EP2014/050025
§ 371 (c)(1),
(2) Date: Jul. 16, 2015

(87) PCT Pub. No.: WO2014/111275
PCT Pub. Date: Jul. 24, 2014

(65) Prior Publication Data
US 2015/0361115 A1   Dec. 17, 2015

(30) Foreign Application Priority Data

Jan. 17, 2013 (DE) .................... 10 2013 200 675

(51) Int. Cl.
| | | |
|---|---|---|
| *C07F 7/14* | (2006.01) | |
| *C07F 7/08* | (2006.01) | |
| *C07F 7/12* | (2006.01) | |
| *B01J 21/04* | (2006.01) | |
| *B01J 23/02* | (2006.01) | |
| *B01J 27/125* | (2006.01) | |
| *B01J 35/10* | (2006.01) | |

(52) U.S. Cl.
CPC ............... *C07F 7/125* (2013.01); *B01J 21/04* (2013.01); *B01J 23/02* (2013.01); *B01J 27/125* (2013.01); *B01J 35/1019* (2013.01); *B01J 35/1042* (2013.01); *C07F 7/08* (2013.01); *C07F 7/126* (2013.01); *C07F 7/14* (2013.01)

(58) Field of Classification Search
CPC ........................................ C07F 7/14; C07F 7/08
USPC ........................................................ 556/469
See application file for complete search history.

(56) References Cited

U.S. PATENT DOCUMENTS

| | | |
|---|---|---|
| 3,793,357 A | 2/1974 | McEntee |
| 4,888,435 A | 12/1989 | Chadwick et al. |
| 6,175,029 B1 | 1/2001 | Colin |
| 2003/0109735 A1 | 6/2003 | Tsukuno et al. |
| 2011/0196165 A1 | 8/2011 | Mautner et al. |

FOREIGN PATENT DOCUMENTS

| | | |
|---|---|---|
| DE | 2351258 | 5/1974 |
| DE | 102008043331 A1 | 5/2010 |
| EP | 0 146 148 A1 | 6/1985 |

*Primary Examiner* — Elvis O Price
(74) *Attorney, Agent, or Firm* — Brooks Kushman P.C.

(57) ABSTRACT

Alkyl chlorosilanes from the manufacture of dialkyldichlorosilanes are rearranged in continuous fashion to dialkyldichlorosilane by a rearrangement reaction in a moving bed reactor employing a solid alumina catalyst containing aluminum chloride, spent catalyst being continuously removed from the reactor.

16 Claims, No Drawings

METHOD FOR PRODUCING ALKYL CHLOROSILANES BY WAY OF REARRANGEMENT REACTIONS

CROSS REFERENCE TO RELATED APPLICATIONS

This application is the U.S. National Phase of PCT Appln. No. PCT/EP2014/050025 filed Jan. 2, 2014, which claims priority to German Application No. 10 2013 200 675.6 filed Jan. 17, 2013, the disclosures of which are incorporated in their entirety by reference herein.

BACKGROUND OF THE INVENTION

1. Field of the Invention

The invention relates to a process, for preparing alkylchlorosilanes which may include hydrogen, in the presence of an alumina catalyst which proceeds continuously in a moving bed reactor.

2. Description of the Related Art

The preparation of alkylchlorosilanes by direct synthesis (Müller-Rochow synthesis) results, apart from the main dialkyldichlorosilane product, in further silanes such as tetraalkylsilane, trialkylchlorosilane, and alkyltrichlorosilane inter alia, for which there is varying demand and, in the event of a surplus, a possible use is required. In the distillation of the crude silane mixture from the direct synthesis of alkylchlorosilanes and chlorosilanes, first runnings and intermediate fractions are also obtained, which cannot be utilized directly for further processing.

For instance, it is well known from the literature that aluminum chloride in all forms catalyzes the rearrangement of alkyl chlorosilanes, even on support materials such as aluminas. These are processes in fixed bed reactors. In US20030109735, the conversion in the trimethylsilane+methyltrichlorosilane or trimethylchloro-silane+methyltrichlorosilane reactions is improved by adding magnesium oxide, for example, to the aluminum chloride. DE 2351258 describes the addition of promoters to such reactions, these minimizing the discharge of aluminum chloride from the reaction vessel. U.S. Pat. No. 6,175,029, in contrast, describes the use of very pure alumina as a catalyst. EP 0146148 also describes the use of zeolites as a catalyst for the rearrangements. DE 102008043331 describes the improvement of the conversion level in a fixed bed reactor through an addition of magnesium, copper or zinc in the alumina.

Fixed bed reactors have the disadvantage that the catalyst exchange becomes ever more technically demanding with increasing reactor size. An environmentally friendly emptying operation requires a deactivation, for example, in order to prevent outgassing of silanes and hydrogen chloride as a result of hydrolysis or ingress of air. Equally, some silanes having hydrogen on the silicon self-ignite on ingress of air. The refilling of a shell and tube reactor in particular is complicated by the fact that all the tubes have to have the same pressure differential to assure optimal catalyst exploitation.

SUMMARY OF THE INVENTION

The invention provides a process for preparing silanes of the general formula (1)

$$R_aH_bSiCl_{4-a-b} \quad (1),$$

in which mixtures of silanes of the general formulae (2) and (3)

$$R_cSiCl_{4-c} \quad (2),$$

$$R_dH_eSiCl_{4-d-e} \quad (3),$$

where
R is an alkyl radical having 1 to 6 carbon atoms,
a has the values of 1, 2 or 3,
b has the values of 0 or 1,
c has the values of 1, 2, 3 or 4,
d has the values of 0, 1 or 2 and
e has the values of 0, 1 or 2, are converted continuously in a moving bed reactor in the presence of an alumina catalyst containing 1 to 10 parts by weight of aluminum chloride per 100 parts by weight of alumina.

DETAILED DESCRIPTION OF THE PREFERRED EMBODIMENTS

These are rearrangement reactions of silanes of the general formulae (2) and (3) to silanes of the general formula (1).

In the moving bed reactor, the catalyst is moved and spent catalyst is discharged continuously at the same time. There is thus a constant exchange of the catalyst. Emptying and refilling of the reactor and the associated problems are avoided.

Examples of moving bed reactors include sliding bed reactors, screw reactors and fluidized bed reactors. In the case of the moving bed and sliding bed reactor, the catalyst moves by virtue of gravity as a fixed bed through the reactor and leaves it at the reactor base. In the screw reactor, the catalyst is moved through the reactor by means of a screw and leaves it at its end through an orifice. In the case of the fluidized bed reactor, spent catalyst is discharged continuously with the gas stream and can be separated out, for example, by means of cyclones.

The deactivated catalyst removed from these reactors can then be disposed of or regenerated either batchwise or continuously in separate plants, and then fed back to the reaction. The product mixture is worked up by known methods.

Preferably, the R radical has 1 to 3 carbon atoms. More particularly, the R radical is a methyl or ethyl radical.

Preferred products are dialkyldichlorosilane, trialkylchlorosilane and alkylhydrochlorosilanes.

Preferably, the rearrangement reactions [1] to [11] conducted are:

$$CH_3SiCl_3 + H_2SiCl_2 \rightarrow CH_3HSiCl_2 \quad [1]$$

$$(CH_3)_2SiCl_2 + H_2SiCl_2 \rightarrow CH_3HSiCl_2 + (CH_3)_2HSiCl \quad [2]$$

$$(CH_3)_3SiCl + H_2SiCl_2 \rightarrow CH_3HSiCl_2 + (CH_3)_2HSiCl \quad [3]$$

$$(CH_3)_3SiCl + (CH_3)SiCl_3 \rightarrow (CH_3)_2SiCl_2 \quad [4]$$

$$(CH_3)_3SiCl + (CH_3)HSiCl_2 \rightarrow (CH_3)_2HSiCl \quad [5]$$

$$(CH_3)_3SiCl + HSiCl_3 \rightarrow (CH_3)_2SiCl_2 + CH_3HSiCl_2 + (CH_3)_2HSiCl \quad [6]$$

$$(CH_3)_3SiCl + SiCl_4 \rightarrow CH_3SiCl_3 + (CH_3)_2SiCl_2 \quad [7]$$

$$CH_3SiCl_3 + (CH_3)_4Si \rightarrow (CH_3)_2SiCl_2 + (CH_3)_3SiCl \quad [8]$$

$$(CH_3)_4Si + SiCl_4 \rightarrow CH_3SiCl_3 + (CH_3)_2SiCl_2 + (CH_3)_3SiCl \quad [9]$$

$$(CH_3)_4Si + (CH_3)_2SiCl_2 \rightarrow (CH_3)_3SiCl \quad [10]$$

$$(CH_3)_4Si + HSiCl_3 \rightarrow (CH_3)_2SiCl_2 + (CH_3)_3SiCl + (CH_3)_2HSiCl \quad [11]$$

The alumina may be alpha-alumina, or preferably, gamma-alumina.

Preferably, the alumina catalyst has 2 to 8, especially 3 to 6, parts by weight of aluminum chloride per 100 parts by weight of alumina.

The aluminum chloride content of the alumina catalyst can be generated by treatment of alumina by known methods with hydrogen chloride, for example, and subsequent drying in a hot gas stream, under reduced pressure or with $(CH_3)_3SiCl$.

The alumina catalyst may contain up to 10% by weight of a metal oxide selected from magnesium oxide, copper oxide, zinc oxide and mixtures thereof. Preferably, the alumina catalyst includes 0.5% to 5% by weight of the metal oxide. Metal oxides or mixed oxides used may be any oxides or mixed oxides of the metals magnesium, copper and zinc. Particular preference is given to magnesium oxide.

Preferably, the alumina catalyst has a BET surface area of at least 100 $m^2/g$, more preferably at least 200 $m^2/g$, and preferably at most 600 $m^2/g$.

Preferably, the alumina catalyst has an Hg pore volume of at least 0.2 $cm^3/g$, more preferably at least 0.5 $cm^3/g$, and most preferably at most 1.5 $cm^3/g$.

The particle size distribution of the alumina catalyst should be chosen for achievement of optimal operating conditions for the particular reactor type, for example for attainment of a well-defined fluidized bed.

Preferably, the alumina catalyst for use in a fluidized bed reactor has a particle size distribution of 20 to 1000 μm, more preferably of 30 to 5000 μm and especially of 40 to 250 μm. For use in a moving bed reactor, preference is given to pellets of a diameter of from 1-10 mm.

The process is preferably conducted at at least 200° C., more preferably at least 300° C., and especially at least 350° C., and preferably at most 600° C., more preferably at most 550° C., and especially at most 520° C. The process is preferably conducted at at least 0.5 bar, more preferably at least 2 bar, and especially at least 4 bar, and preferably at most 30 bar, more preferably at most 10 bar, and especially at most 7 bar.

Since silanes of the general formula (3) in which e has the value of 1 or 2 also promote reactions between silanes of the general formulae (2) and (3) in which e in the general formula (3) has a value of 0, preference is given, in the case of such reactions, to adding silane of the general formula (3) in which e has the value of 1 or 2. Silanes of the general formula (3) in which e has the value of 1 or 2 therefore have cocatalytic action.

The proportion of silane of the general formula (3) in which e has the value of 1 or 2 in the mixture of silanes of the general formulae (2) and (3) is preferably at least 0.5% by weight, more preferably at least 5% by weight, and especially at least 10% by weight.

The silanes of the general formula (3) in which e has the value of 1 or 2 that are used may also be used in the form of mixtures, for example in the form of distillate fractions in which, for example, $CH_3HSiCl_2$, $(CH_3)_2HSiCl$ and $HSiCl_3$ are present.

The alumina catalyst is preferably prepared by treating alumina containing the metal oxides with hydrogen chloride, preferably at least 100° C., more preferably at least 180° C., and most preferably at most 250° C.

Subsequently, the alumina catalyst thus prepared is dried in the hot gas stream, preferably under reduced pressure, or with trimethylchlorosilane.

All the above symbols in the above formulae are each defined independently of one another. In all the formulae, the silicon atom is tetravalent.

In the examples and comparative examples which follow, unless stated otherwise in each case, all the amounts and percentages stated are based on weight and all the reactions are conducted at a pressure of 1 bar (abs.).

For the silanes in the tables, the following abbreviations were used:
TCS: trichlorosilane
M1: methyltrichlorosilane
M2: dimethyldichlorosilane
M3: trimethylchlorosilane
HM: methylhydrodichlorosilane The examples which follow are based on a continuously operated glass fluidized bed reactor heated electrically to 500° C., having diameter 30 mm and length 450 mm, with an upstream reactant evaporator in the case of operation without elevated pressure. The gas distributor used was a glass frit. The fluidized material used was 100 mL (46 g) of a screen fraction of 50-180 μm gamma-alumina with 1% by weight of Mg as oxide, having a BET surface area of 276 $m^2/g$ and an Hg pore volume 0.89 $cm^3/g$, in which 4.5% by weight of aluminum chloride had been formed from the alumina beforehand by treatment in a hydrogen chloride stream.

The products were analyzed by means of GC (calibrated for % by mass).

Example 1

Here, the space-time yields of M2 silane in the reactions of M1+M3=1:1 mol from DE 102008043331 (not in accordance with the invention, MgO-containing catalyst at 300° C.; 6.5 bar (abs.)) were compared with the yields in the fluidized bed (in accordance with the invention, with similar MgO-containing catalyst; 1 bar, 500° C.): the catalyst density was assumed to be equal.

|  | Reactant throughput | Reactant molar ratio | Target product |
|---|---|---|---|
| not in accordance with invention | 100 g/h with 230 g of catalyst | 1M1:1M3 + 5% HM | 222 g M2/h*kg of catalyst |
| not in accordance with invention | 500 g/h with 690 g of catalyst | 1M1:1M3 + 5% HM | 261 g M2/h*kg of catalyst |
| in accordance with invention | 80 g/h with 46 g of catalyst | 1M1:1M3 + 5% HM | 339 g M2/h*kg of catalyst |
| in accordance with invention | 80 g/h with 46 g of catalyst | 1M1:1M3 | 285 g M2/h*kg of catalyst |

The cocatalytic action of a silane of the general formula (3) having Si-bonded hydrogen is maintained in the process of the invention.

Example 2

Under the same conditions, M3 is reacted with $SiCl_4$: not in accordance with the invention in a tubular reactor at 6.5 bar (abs.); and at 300° C. and 500° C., 1 bar in accordance with the invention in a fluidized bed:

|  | Reactant throughput | Reactant molar ratio | Target product |
|---|---|---|---|
| not in accordance with invention | 400 g/h with 538 g of catalyst | 1SiCl$_4$:2M3 + 10% HSiCl$_3$ | 235 g M2/h*kg of catalyst |
| in accordance with invention | 95 g/h with 46 g of catalyst | 1SiCl$_4$:1M3 | 361 g M2/h*kg of catalyst |

The invention claimed is:

1. A process for preparing silanes of the formula (1)

$$R_aH_bSiCl_{4-a-b} \quad (1),$$

in which mixtures of silanes of the formulae (2) and (3)

$$R_cSiCl_{4-c} \quad (2),$$

$$R_dH_eSiCl_{4-d-e} \quad (3),$$

where
R is an alkyl radical having 1 to 6 carbon atoms,
a is 1, 2 or 3,
b is 0 or 1,
c is 1, 2, 3 or 4,
d is 0, 1 or 2 and
e is 0, 1 or 2,
are converted continuously in a moving bed reactor in the presence of an alumina catalyst containing 1 to 10 parts by weight of aluminum chloride per 100 parts by weight of alumina, wherein the catalyst is moved in the moving bed reactor and spent catalyst is discharged from the reactor during the process.

2. The process of claim 1, in which the R radicals are methyl or ethyl radicals.

3. The process of claim 1, in which the alumina catalyst has a BET surface area of at least 100 m²/g.

4. The process of claim 2, in which the alumina catalyst has a BET surface area of at least 100 m²/g.

5. The process of claim 1, in which the alumina catalyst has a pore volume of at least 0.5 cm³/g.

6. The process of claim 2, in which the alumina catalyst has a pore volume of at least 0.5 cm³/g.

7. The process of claim 3, in which the alumina catalyst has a pore volume of at least 0.5 cm³/g.

8. The process of claim 4 in which the alumina catalyst has a pore volume of at least 0.5 cm³/g.

9. The process of claim 1, in which the alumina catalyst contains up to 10% by weight of one or more of magnesium oxide, copper oxide, and zinc oxide.

10. The process of claim 3, in which the alumina catalyst contains up to 10% by weight of one or more of magnesium oxide, copper oxide, and zinc oxide.

11. The process of claim 5, in which the alumina catalyst contains up to 10% by weight of one or more of magnesium oxide, copper oxide, and zinc oxide.

12. The process of claim 1, in which the reaction takes place at a temperature of from 200° C. to 600° C.

13. The process of claim 1, in which the moving bed reactor is a sliding bed reactor, a screw reactor or a fluidized bed reactor.

14. The process of claim 1, wherein fresh catalyst is added to the reactor during the process to replace the spent catalyst removed.

15. The process of claim 14, wherein at least a portion of the fresh catalyst comprises regenerated spent catalyst.

16. The process of claim 1, wherein the spend catalyst is removed continuously during the process.

* * * * *